United States Patent [19]

Hirabayashi et al.

[11] 4,259,072
[45] Mar. 31, 1981

[54] CERAMIC ENDOSSEOUS IMPLANT

[75] Inventors: Masaya Hirabayashi, Yokaichi; Haruyuki Kawahara, Moriguchi, both of Japan

[73] Assignee: Kyoto Ceramic Co., Ltd., Japan

[21] Appl. No.: 60,649

[22] Filed: Jul. 25, 1979

Related U.S. Application Data

[63] Continuation-in-part of Ser. No. 787,623, Apr. 4, 1977, abandoned.

[51] Int. Cl.³ .......................... A61C 8/00; A61F 1/24
[52] U.S. Cl. ................................... 433/173; 433/201; 3/1.9; 3/1.913; 128/92 C; 128/92 CA
[58] Field of Search ............... 3/1, 1.91, 1.911, 1.912, 3/1.913, 1.9; 32/10 A, 10 R; 128/92 R, 92 C, 92 CA; 433/173, 201

[56] References Cited

U.S. PATENT DOCUMENTS

| | | | |
|---|---|---|---|
| 2,857,670 | 10/1958 | Kiernan, Jr. | 32/10 A |
| 3,314,420 | 4/1967 | Smith et al. | 3/1 |
| 3,787,900 | 1/1974 | McGee | 3/1 |
| 3,852,045 | 12/1974 | Wheeler et al. | 3/1 |
| 3,906,550 | 9/1975 | Rostoker et al. | 3/1.912 |
| 3,918,100 | 11/1975 | Shaw et al. | 32/10 A |
| 3,934,347 | 1/1976 | Lash et al. | 32/10 A |
| 3,943,576 | 3/1976 | Sirash | 3/1 |
| 4,016,651 | 4/1977 | Kawahara et al. | 32/10 A |
| 4,171,544 | 10/1979 | Hench et al. | 128/92 C |

FOREIGN PATENT DOCUMENTS

| | | | |
|---|---|---|---|
| 2154272 | 5/1973 | Fed. Rep. of Germany | 32/10 A |
| 2401323 | 7/1974 | Fed. Rep. of Germany | 32/10 A |
| 2419080 | 11/1975 | Fed. Rep. of Germany | 32/10 A |
| 2540077 | 4/1976 | Fed. Rep. of Germany | 32/10 A |
| 2615116 | 10/1976 | Fed. Rep. of Germany | 32/10 A |
| 49-45920 | 5/1974 | Japan | 32/10 A |
| 1083769 | 9/1967 | United Kingdom | 32/10 A |

OTHER PUBLICATIONS

Hulbert, S. F. et al., J. Biomed. Mater. Res. Sym., No. 4, pp. 1-23 (1973).
Homsy, C. A. et al., Clin. Orthopaedics, No. 89, pp. 220-235 (1972).

Primary Examiner—R. E. Serwin
Attorney, Agent, or Firm—Richard H. Zaitlen

[57] ABSTRACT

This disclosure relates to an endosseous implant for use in dental and orthopedic treatment. The implant is a composite structure made of a combination of an outer ceramic member and an inner ceramic core member bonded together by glass cement. After being implanted, new bone tissue and new connective tissue penetrate into the outer member to form a net-like root structure therein, thereby increasing the stability of the implant and at the same time the outer member is reinforced by the inner core member.

23 Claims, 12 Drawing Figures

FIG.4
FIG.5
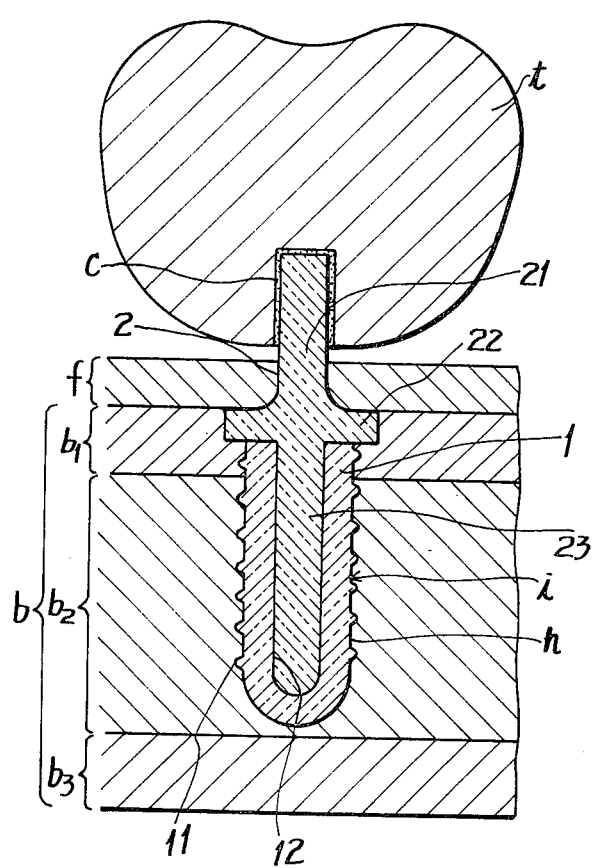
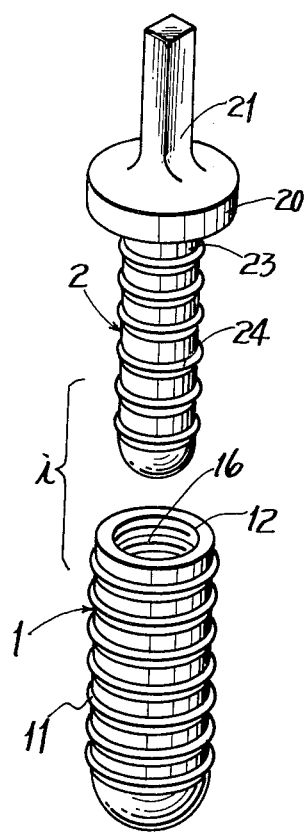

CERAMIC ENDOSSEOUS IMPLANT

CROSSREFERENCE TO RELATED APPLICATION

This application is a continuation-in-part of U.S. patent application No. 787,623, filed Apr. 4, 1977, now abandoned.

BACKGROUND OF THE INVENTION

1. Field of the Invention

This invention relates to improvements in an endosseous implant used in dental and orthopedic treatment.

2. Prior Art

Surgical techniques involving the use of an implant (screw implant, blade implant, pin implant, etc.) into bone tissue are extensively utilized in dental and orthopedic surgery as a result of the progress made in somatological engineering.

In prior art endosseous implant, the emphasis was on increasing the strength of the implant in the structure. For instance, the present inventors relied on structural considerations for the implant of the previous U.S. Patent Application Ser. No. 550,186 wherein a nut was fitted over the head portion of a screw type implant (and, if necessary, the bottom portion of the implant passed through bone tissue). The device was screwed into the bone tissue and the screw-tightening force of the nut pressed the implant into contact with the bone tissue so as to cause the implant to resist the repeated external force to which the implant was then subjected.

It is an object of the present invention to obtain stabilized post-implantation strength from a binding force between the tissue of the living being and the implant. This binding force is a result of new bone and connective tissue of the living infiltrating deep into the implant surface. In this manner, proliferation and ossification of the bone and connective tissues in a net-like working arrangement is achieved. Another object of the invention, as will become apparent from the description that follows, is to regulate the amount of the incoming new bone and connective tissues by the selection of opening diameters of the micro-apertures located in the ceramic material and in a biodegradable material, and making either of the tissues larger in quantity than the other or making both of them uniform in quantity. In this manner the rigid bonding force inherent in the bone tissue and the elastic bonding force inherent in the connective tissue are brought into conformity with the state of the affected region in which the implant is to be set.

SUMMARY OF THE INVENTION

In order to achieve these and other objects, the invention includes a combined structure of two members in the form of a ceramic outer member and a ceramic inner core member. Structural considerations allow for penetration of the outer member by new bone and connective tissue. The composite structure is used to compensate for a possible reduction in the mechanical strength of the outer member due to its inherent structure. Added strength is achieved with the aid of the core material which is either rigid and close ceramics, or single crystal ceramics. Two species are briefly mentioned as a means provided by the other member for permitting the penetration of such new bone tissue and new connective tissue thereinto. In one species the surface of the outer member in contact with a bone tissue has microapertures distributed in a net-like working arrangement over the area extending from the surface to the inside of the member, the micro apertures suitable in diameter to allow penetration of new bone tissue and connective tissue into it. In the other species the outer member contains a biodegradable material able to be broken down by the bone tissue into a linking form from the surface to the inside of the member.

The invention will now be described with reference to preferred embodiments thereof, shown by way of example only, reference being made to the accompanying drawings.

BRIEF EXPLANATION OF THE DRAWINGS

FIG. 4 is a sectional view showing a prosthetic structure of an artificial tooth using the implant of the invention;

FIG. 5 is an exploded perspective view showing a dental screw type implant in another embodiment of the invention;

DETAILED DESCRIPTION OF THE PREFERRED EMBODIMENTS

Figure 1:
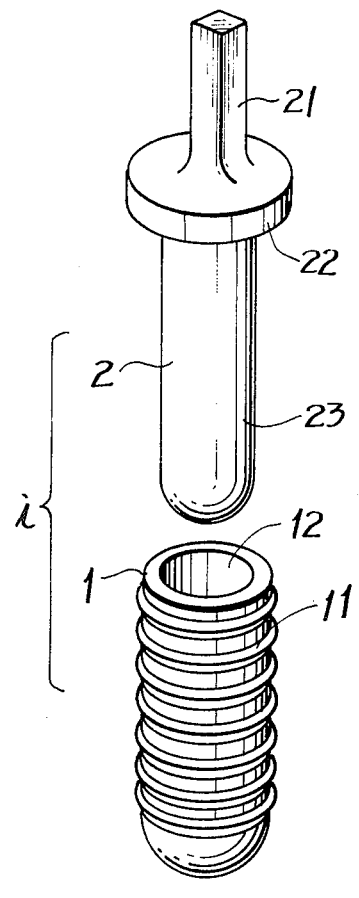
FIG. 1 is an exploded perspective view showing a dental screw type implant in one embodiment of the invention.
Figure 2:
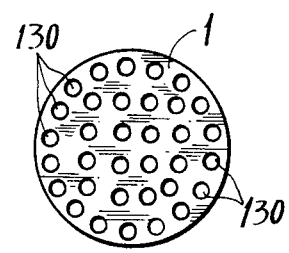
FIG. 2 is a microscopically enlarged diagrammatic view showing the surface of the outer member.

In the drawings, FIGS. 1 through 4 show various embodiments of the invention included under the first species. FIGS. 5 through 10 show embodiments of the invention included under the second species. FIGS. 1 through 11 show implants for use in dental endosseous implantation, and FIG. 12 shows an implant for use in artificial joint utilized in orthopedic surgery.

Figure 3:
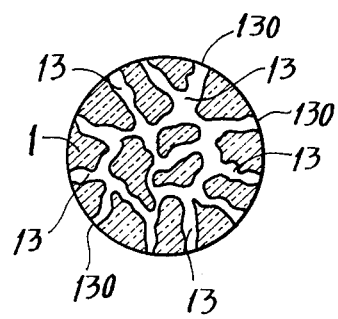
FIG. 3 is a microscopically enlarged sectional diagrammatic view showing the inside of the outer member.

Referring now in detail to the invention in conjunction with the drawings, the implant of the invention comprises an outer member 1 and an inner core member 2. Both members 1 and 2 are tightly bonded together into a combined assembly, i.e., a composite structure. In the embodiment illustrated in FIGS. 1 through 4, both the outer member 1 and the inner core member 2 are made of polycrystalline sintered ceramics, both members being sintered or cemented into one body. The outer member 1 is a slender cylindrical body and may be formed on the outer periphery with threads 11. The inner core member 2 is formed at the top and thereunder respectively with an artificial tooth receiving portion 21, a flange 22, which is at least not smaller in outer diameter than the outer member 1, and a post portion 23 adapted to be closely fitted into a cavity 12 in the outer member 1. Means are provided in the outer member 1 for permitting the penetration of a new bone tissue and a new connective tissue thereinto. This is shown in FIG. 3 as micro-apertures 13. The apertures 13 are located in the outer member 1 in net-like working arrangement (in a cubic net-like state) from the surface portion toward the inside of the outer member 1, and most of the openings 130 of the micro-apertures 13 in the surface portion are arranged to be on the order of 100 $\mu$m (0.1 mm) in diameter, preferably in the range of 100–500 $\mu$m in diameter so as to permit the passage of the new bone tissue thereunder. Alternatively, they may be in the range of 20–100 $\mu$m in diameter so as to permit the passage of the new connective tissue therethrough.

Although the ceramics used in the prior art implant of ceramics were higher in affinity to the new bone and new connective tissues than metal and plastics, the new tissues could not penetrate deep into the implant and fix themselves thereto. The reason is that, since ceramics forming the implant are close in texture and lacking in permeability, the prior art ceramics afford no room for the new bone and connective tissues to penetrate therethrough. On the other hand, when unglazed (porous) ceramic is used, such ceramics permit the existence of very small apertures inside thereof. However, it is also equally true that such apertures are very small, i.e., less than 10 $\mu$m. Therefore, it is virtually impossible for the new bone and connective tissue to penetrate therethrough. As will later be described, according to the findings of the present inventors, it is necessary that the apertures be larger than 200 $\mu$m (0.2 mm) in effective opening diameter to permit new bone tissue to penetrate through the apertures. Furthermore, it is necessary that in the case of the dental implant that the apertures be in the range of in the range of 200–700 $\mu$m, preferably 300–500 $\mu$m in effective diameter of opening, and that in the case of the orthopedic implant, the apertures be in the range range of 200 $\mu$m–5 mm, preferably 300–500 $\mu$m in effective opening diameter. In order for the new connective tissue to penetrate through the micro-apertures, their openings must be far smaller in diameter and must be in the range of 20–100 $\mu$m. In the present invention, it is proposed on the basis of the above findings, that the micro-apertures 13 be larger than 20 $\mu$m in the diameter of opening. In the case of the dental implant they should be in the range of 20–700 $\mu$m in order to permit both new bone and connective tissues to penetrate in larger percentage. The penetration of the new bone tissue through the implant has the characteristic of imparting rigid bonding to the implant. The penetration of connective tissue through the implant has the characteristic of imparting elastic bonding to the implant because such tissue is fibrous and high in elasticity. Accordingly, when the implant is subjected to overstress, it is necessary that the new connective tissue penetrate in larger percentage through the implant, and conversely when the implant is subjected to less stress and rigid bonding is required, all that is necessary is to make it possible for the new bone tissue to penetrate in larger percentage through the implant. Alternatively, when it is desired for both the new bone tissue and connective tissue to penetrate in equal percentage through the implant, it is necessary to afford an equal opportunity for both tissues to penetrate the implant. Regulation of the penetration opportunity of both tissues, needless to say, depends upon the distribution percentage chosen for the two opening diameters (20–100 $\mu$m and 200–700 $\mu$m).

A net-like working structure provided by the micro-apertures 13 of the type described must be formed at least on the outer surface of the member 1 in contact with a bone tissue. As illustrated in FIGS. 1 and 3, the structure has been formed with micro-apertures 13 over the entire thickness of the member 1. Furthermore, the micro-aperture openings 130 on the member 1 outer surface must have diameters in the ranges described above, but the pore diameters inside the member 1 need not necessarily be limited to the ranges described. The reason for this is that even if there may be some differences in aperture diameter, the new bone and connective tissues which penetrate through the openings in the surface of the member 1 can find their way into the inner part. It should be understood that the contact surface of the outer member 1 in which the apertures 13 are provided need not necessarily range over that entire area over which the member 1 comes into contact with the bone tissue, but may cover most of the area. Likewise, the limited range in the opening diameters need not necessarily cover all the diameters of the openings located in the contact surface of the member 1 but may cover most part of the limited range. The porosity of outer member 1 suitable for the apertured structure is properly in the range of 20–50%, and penetration of the new bone and connective tissues is reduced in amount when the porosity is below this range. When the porosity is above this range, machining of the member 1 such as thread cutting becomes difficult because the member increases in brittleness. The method of obtaining a porous structure member 1 having such a porosity is preferably instituted by sintering a mixed material, produced by mixing a vanishing material with a ceramic material. The vanishing material is then burnt out or vaporized from the ceramics, and vanishes and leaves no ashes at all or leaves such ashes, if any, which are quite harmless to the living being. In this manner the pores are formed. Such vanishing materials include polyethylene spherical bodies, acrylate resin fiber chop, and the like.

The inner core member 2 is intended to increase the mechanical strength of the outer member 1 of a porous structure, and accordingly, the material of the member 2 must be solid and strong. The inner core member 2 in this embodiment may be made of a polycrystalline sintered body of ceramics and is shown wherein two members 1 and 2 are sintered into one body with a post portion 23 left inserted into a cavity 12 of the member 1. On the second species shown in FIG. 5, it is possible also to bring the inner core member 2 into mechanical engagement by threads with the outer member 1. In the case of the first embodiment wherein both members are sintered into one body, the two members are, in principle, placed under conjugate sintering conditions. In the second embodiment, the inner core member 2 may be a single crystal body of alumina, and has no such conjugate conditions. Also, in the second embodiment both members 1 and 2 may be bonded to each other by use of a suitable binder, instead of the threaded engagement.

According to an initial object of the inner core member 2, the member should desirably be a single crystalline body which is far superior in strength to polycrystalline ceramics.

A solid core of polycrystalline ceramics, even if it is polished, is on the order of 2500–3500 kg/cm$^2$ in bending strength. In this respect, the solid core of polycrystalline ceramics is far inferior to that of metal. Even though metal is superior in mechanical strength, metal has a great disadvantage in point of practical application in that it has a harmful effect on the human body. Single crystalline alumina ceramics, when used as a solid core, may be as much as several times higher in mechanical strength than polycrystalline ceramics and equal to or higher than metal. Moreover, because single crystal is superior in flexibility to polycrystalline ceramics, the single crystal is highly reliable also in bending strength, which prevents the breaking of an implant due to flexion of the natural bone around the implant.

The member 2 also includes a flange portion 22 preferably larger in outer diameter than the outer member 1. This is apparent from the prosthetic structure in FIG. 4, and is based on the idea of preventing bacilli from invading a hole h of a bone tissue b after an operation by covering the opening of the top portion of the hole h with the flange 22.

A description of dental prosthetic procedures according to the embodiment described above will now be given with reference to FIG. 4. A gingival flap f is cut open, a tap hole h is provided in a bone tissue b and an implant i of the invention is screwed into the hole h. The bone tissue b includes hard tissues $b_1$ and $b_3$ and a soft tissue $b_2$ therebetween. In the embodiment shown, the implant i does not reach the lower hard tissue $b_3$, but the bottom end of the implant i stops in the soft tissue $b_2$. If it is necessary to fix the implant i to the inside of the bone tissue b, a nut (not shown), which enables the implant i to be fixed to the upper hard tissue $b_1$, is threadedly mated with the implant i and an artificial tooth t is fitted over the top of the implant i through cement c.

The embodiment described above provides an inventive implant i, imbedded in the bone tissue b, in which the surface of the outer member 1 in contact with the bone tissue has numerous openings 130 for micro-apertures, most of whose diameters are greater than 20 μm. Because of the apertures 13, it is possible for the outer member 1 to have gas permeability at least on its surface side to permit the penetration of the bone tissue b, particularly the new bone tissue and new connective tissue of the upper hard bone tissue $b_1$, through the openings 130 into the inner part of the outer member 1. In response thereto, the tissues thus penetrated dispersedly drives the gas existing inside the micro-apertures 13 ($CO_2$ and $NH_3$ are especially abundant in a living being) through openings 130 into the bone tissue b. Penetration of the new bone and connective tissues into the member 1 in such a responsive relation is thus enhanced. This causes the tissues to form a net-like root structure in every part of the member 1 over a long period of time. Thus, as in the case of the prosthetic structure shown in FIG. 4, the member 1 and the bone tissue b, can develop into very firmly bonded relation because of the net-like structure of the roots of the new bone and connective tissues which have extended throughout the member 1. Accordingly, if the outer member 1 should be cracked after the operation, the new bone and connective tissues which have penetrated into the member 1 serve to support the cracked member 1. In this manner the cracked member is prevented from being further cracked. In addition, the new bone and connective tissue serves to strengthen the support characteristics of member 1. In the embodiment in FIG. 4, the direction in which the new tissues penetrate through the member 1 is generally at right angles to the axial direction of the inner core member 2, and accordingly, marked improvement is made in the resistance of the implant i to the accluding impact centered on the implant i. Additionally, since the implant i of the invention is made of ceramics, it is free from toxic properties and does not produce adverse effects on the human body even if implanted in the bone tissue b over a longer period of time. Since the implant i is excellent in durability, it does not cause any chemical deterioration due to secretions. Finally, since the outer member 1 of the invention is reinforced internally with the inner core member 2 of compact polycrystalline body of ceramics or single crystalline ceramics, the implant i provides no possibility of being broken or deformed by the repeated accluding impacts given thereto. Thus it can stand long time use in its implanted state.

Figure 6:
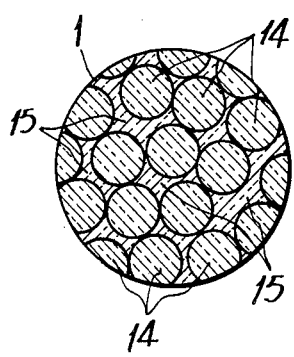
FIG. 6 is a microscopically enlarged diagrammatic sectional view showing the inside of the wall thickness of the outer member.
Figure 7:
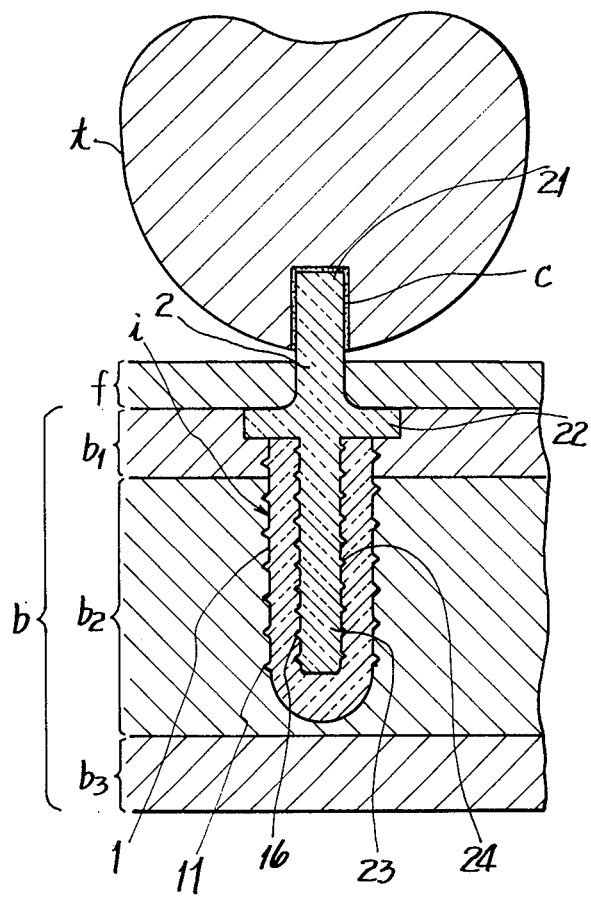
FIG. 7 is a longitudinal sectional view showing the prosthetic structure of an artificial tooth using the implant of the second embodiment of the invention.

A description will now be given of the second species of the invention with reference to FIGS. 5 through 10, wherein like parts are represented by the same reference characters and space. Means for permitting the penetration of the new bone tissue and new connective tissue in this embodiment is shown as a material 14 which is degraded by the new bone and connective tissues that find their way into the member 1. The material 14 takes the place of the micro-apertures 13 in the first embodiment. More specifically, the outer member 1 in FIGS. 5 and 7 includes an apatite sintered body in the form of new biodegradable material 14 in the ceramics of the member 1. More particularly, the outer member 1 in this embodiment is a sintered complex (the term "complex" means that the body produced is made of a plurality of materials, and is different from the term "composite" in the composite structure hereinbefore used) consisting mainly of ceramics 15 and an apatite sintered body 14. The apatite sintered body 14 in FIG. 6 is an aggregate which retains the form of a sphere, polyhedron, fibrous body, etc. and whose grains are linked to one another in a net-like working arrangement. The ceramics 15 in FIG. 6 are an aperture-filling body continuously linked throughout the aggregate for filling the apertures between the grains of the aggregate so as to form a net-like working structure.

Apatite is a general term for a substance represented by chemical formula $A_{10}(PO_4)_6 \cdot X_2$. calcium phosphate based hydroxy-apatite represented by $Ca_{10}(PO_4)_6 \cdot (OH)_2$ is the one which has been found to be most closely related to a living being. This hydroxy-apatite is the chief constituent of minerals of bones and teeth of a vertebrate animal. The hydroxy-apatite can be synthesized and also can be obtained by removing organic matter (protein, polysaccharide, etc.) from the bones and teeth of a living being through combustion, through melting, or through dissolving. The former is termed synthetic apatite and the latter is termed bioapatite.

Figure 9:
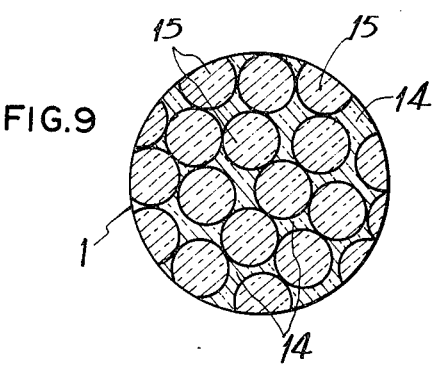
FIG. 9 is a microscopically enlarged diagrammatic view showing the pre-implantation state of the inside of the outer member of another embodiment of the invention.

The apatite in this embodiment may contain either of the above two kinds of apatite. This powder is sintered under pressure into an apatite sintered body 15. It is desirable to have the main constituent of this apatite sintered body to be calcium triphosphate $Ca_2(PO)_4$, which has the property of being physiologically dissolved and absorbed (the term "physiologically dissolve and absorb" will hereinafter be referred to as the term "biodegrade") inside a living being and substituting the tissue of the living being for itself. In a first example, outer member 1 is made exclusively of apatite sintered body 15 and in a second example, outer member 1, as seen in FIGS. 6 and 9, consists of a combination of a sintered body of apatite and a sintered body of ceramics 15, preferably alumina ceramic. The apatite sintered body 14 in FIG. 6 is a solid nonporous structure in which the body 14 extends in a net-like working arrangement from the surface region of the outer member through the wall thickness to the inside thereof, thus filling the micro-apertures in this aggregate with ceramics 15. In another embodiment of the second species, the relation between the apatite sintered body 14 and the aperture-filling ceramics 15 is reversed. In this case, the sintered body 14 extends from the surface to part of its wall thickness. Penetration of the new tissues into the member 1 is made possible by the fact that the optimum grain size of the apatite sintered body 14 which permits the body 14 to be biograded by the new bone and connective tissues, measures more than 20 $\mu$m in the area in which the body 14 comes into contact with the new tissues, and more than 10 $\mu$m in the narrowest portion. Accordingly, in the embodiment illustrated, the spherical grains of apatite sintered body 14 which are in contact with each other are designed to measure more than 10 $\mu$m in diameter. The shape of apatite sintered body 14 may be optionally selected from the configuration range of sphere, polyhedron, fiber, pellet and the like.

In a modified embodiment of the invention in FIG. 9, the sintered apatite body which becomes a filler is arranged to be more than 10 $\mu$m wide on the connecting neck portion. Accordingly, to one method of producing the outer member 1, it is only necessary to compact and sinter apatite powder when the outer member is made exclusively of apatite sintered body 14 above. When it is desired to produce the member 1 of a combined body of apatite sintered body 14 and ceramics 15, the apatite sintered body 14 is mixed with ceramics (not shown) in quantities suitable for the sintered body 14 to the distributed in a net-like working arrangement. The mixture obtained is pressure-compacted and then sintered. Alternatively, apatite powder (not shown) and ceramics 15 in the form of an aggregate consisting of a sintered or semisintered body of ceramics are mixed in such a ratio that the ceramics 15 may be distributed to provide the desired net-like working arrangement, and the resulting mixture is pressure-compacted and sintered. In the above procedures, a molding improver, sintering accelerator, organic binder, grain growth retarder, etc. should be used in accordance with the ceramic sintering process known in the art. The inner core material 2 in the second species is the same as that in the first species. The members 1 and 2 in FIG. 5 are connected integrally with each other by threads, with the result that the cavity 12 of the member 1 is provided with internal thread 16 and the post portion 23 of the core member 2 is provided with external thread 24. The dental prosthetic procedure to be used in this embodiment is substantially the same as that referred to in the preceding embodiment, except for the minor difference that a plastic cap (not shown) is put on the top of the member 1 until the new bone and connective tissues have completed their penetration into the outer member after the member 1 has been threaded engaged in a tap hole h. After the completed penetration, the cap is removed and the core member 2 is brought into threaded engagement with the member 1 thereby relieving the patient of the feelings.

Figure 8:
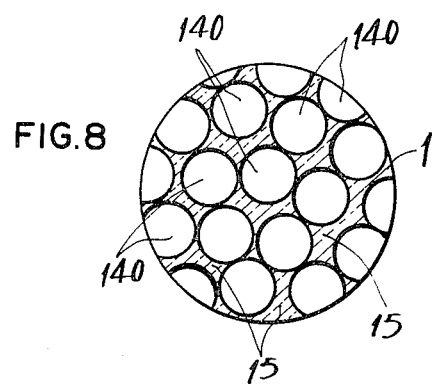
FIG. 8 is a microscopically enlarged diagrammatic sectional view of the inside of the wall thickness of the outer member, the view showing the state in which new bone tissue and connective tissue penetrate into the outer member.
Figure 10:
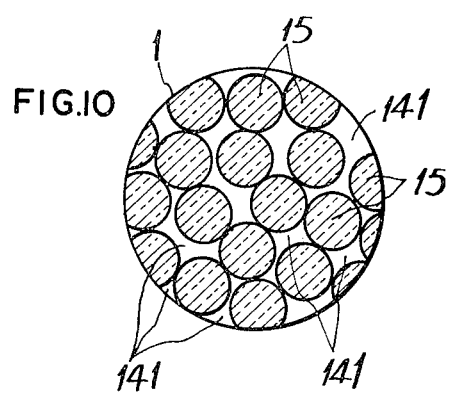
FIG. 10 is a similar view to FIG. 9, and shows the state of the inside of the outer member after the member is implanted.

A description will now be given, with reference to FIGS. 8 and 10, of the new bone and connective tissues, wherein the outer member 1 in this embodiment is biodegraded by the new bone and connective tissues to form a new texture of the member 1. After the member 1 has been implanted in a living being, a net-like working tissue portion is biodegraded by the new bone and connective tissues. In this manner micropores 140 on one hand and a skeleton structure by an aperture-filling ceramic material 15 on the other are formed. This structure is generally spongy as shown in FIG. 8. In actual practice, after the implant i has been implanted in the bone, the new bone and connective tissues penetrate the micropore portions 140 by a biodegradable effect stepwise in the same manner as described above. Alternatively the apatite sintered body 14 forming the aperture-filler is biodegraded to thereby provide micro-apertures 141 as shown in FIG. 10. In this case, the embodiment in FIG. 8 is different from that in FIG. 10 in that in that the former is formed a spongy structure with the new tissues larger in volumetric ratio, the than the latter. This is because when the spherical aggregate and the powder forming the aperture-filling material are pressure compacted, the aggregate measures 5 in diameter and the powder measures 1 in diameter. It will be seen that the embodiment whose material is biodegraded is a spherical body and forms more pores than the material of the other embodiment.

A description will now be given of another embodiment of the second species of the invention as a dental pin implant with reference to FIG. 11. The outer member 1 in this embodiment is made in combination of an apatite sintered body and a ceramic material in the same manner as described. It is provided on the periphery with two ringlike recesses 16 and 16 in a discontinuous relation with each other, instead of external thread. Also, the inner core material 2 of polycrystalline, or a single polycrystalline alumina ceramics as discussed above, is provided with a shoulder 25, instead of the flange 22 used in the preceding embodiments. The outer diameter of the shoulder 25 is designed to be equal to or slightly larger than the diameter of a circular hole h, but both the flange and the shoulder are the same in function. In this embodiment when the pin implant i is implanted in a bone tissue b, new bone tissue penetrates into recesses 16 in a relatively short time and takes root therein. It functions as a retainer of the implant i in place of the screw, and in a period of time, new bone tissue and new connective tissue penetrate into the member 1. Since there is a retaining action already caused by the rigid new bone tissue, one can adjust the diameter of the apatite sintered body to lay more stress on the penetration of the new connective tissue into the member 1 than on that of the new bone tissue. In this manner it is possible for the new connective tissue, high in elasticity, to penetrate in larger quantities, into the outer member 1. The recesses described above may be substituted by one discontinuous helical recess.

The description above has been given of embodiments of the invention with reference to the dental implant. The invention will now be described with reference to an artificial hip joint in FIG. 12. This artificial joint J is designed to join a thighbone $B_1$ to a hip bone $B_2$, and the inner core member 2 is made of a nonporous polycrystalline or single crystalline sintered body of ceramics. The outer member 1 is made of porous ceramics of the first species. Both members 1 and 2 are sintered into one body. The outer member 1 is sleeved over the outer peripheral surface along a post portion 23 out of the core member 2. A joint portion 26 of the member 2 is thereby exposed. Since the post portion 23 of such an artificial hip joint J is not subjected to overstress, it is desired to pay consideration to the diameter of micro-aperture so that the thighbone $B_1$ and the post portion 23 may rigidly be joined. In this way, the new bone tissue may penetrate in larger quantities into the member 1 than the new connective tissue.

Although there is no difference between the first and the second species in the function of the member 1 permitting penetration of the new bone and connective tissues into the member 1, there is a slight difference in advantage between the member of the first and that of the second species. Namely, both species members have to be subjected to perfect sterilization after having been produced, but in the case of the first species it is difficult to thoroughly sterilize the micro-apertures distributed deep into the porous material. Further, because the porous material is relatively coarse in texture on the surface, care must be taken not to cause the coarse surface of the material to scratch or hurt the tissue around the member 1 after implantation. In contract thereto, because the member 1 is of a nonporous material, it is not only easy to sterilize, but also superior in the smoothness of the surface after production.

Mention will now be made of the embodiments of the invention in the following:

EXAMPLE 1 (corresponding to embodiment in FIGS. 1 through 4)

(I) Production of outer member (a) Ceramic material—99.5% (by weight and the same will apply hereinafter) of $Al_2O_3$ (99.8% in purity) in powdered form (0.1–1.5 μm in grain diameter) and 0.5% of sintering accelerator MgO.
(b) Pore-forming material—20% of polyethylene spherical body (200–1000 μm in grain diameter) as against 100% of ceramic material.

The above materials (a) and (b) were mixed by a mixer. The mixture of (a) and (b) thus obtained was poured into a dental endosseous implant forming mold and compacted under a pressure of 500 kg/cm² at normal temperature.

The molded body thus obtained was sintered at a temperature of 1620° C. for two hours. The sintered body thus produced was formed on the surface with openings of micro-apertures between numerous continuous pores, the openings measuring 200–700 μm in diameter. The sintered body was about 30–35% in porosity and was generally a gas-permeable porous polycrystalline sintered body. The periphery of the sintered body was subjected to thread machining, to obtain an outer member.

(II) Production of inner core material

The powder of the above material (a) was subjected to pressure compaction molding to thereby obtain an inner core material having a diameter of 1.8 mm.

(III) Bonding of outer member to core member

After the core member in (II) has been inserted into the outer member in (I) through cement, the members thus bonded were sintered into one body at a temperature of 1600° C. in the open air.

EXAMPLE 2 (corresponding to embodiment in FIGS. 5 through 8).

(I) Production of outer member (a) Aggregate—50% of apatite material which was formed to have a diameter of 30–100 μm and temporarily fired at 1200° C.
(b) Aperture-filling material—50% of powdered alumina. After an aqueous solution of PVA (3% of solid) was added to the above materials (a) and (b), the materials were mixed and stirred, the mixture obtained was pressure-compacted into a pin shape having a diameter of 4 mm and a length of 10 mm and was fired at 1300° C. for one hour, and thereafter the pin was formed on the outer periphery and inside the cavity of its outer member with threads, to obtain an outer member.

(II) Production of core member

Thread cutting was effected on the outer periphery of a core material of single crystal alumina ceramics whose post portion had a diameter of 2 mm.

(III) Bonding of outer member to core member

The outer member in (I) and the core member in (II) were threadedly bonded into one body.

(Follow-up test of implant after the implantation.)

The implant in Example I was used in the prosthetic operation shown in FIG. 4. X-ray photograph of the implant taken about 6 months after the operation showed that primarily a new bone tissue has penetrated in large quantities from the surface of the pin deep into the pin. Also, when the pin in Example 2 was used in the dental prosthetic structure shown in FIG. 7, it was observed that a new connective tissue had found its way in the outer member of the pin after a lapse of 3 months.

Figure 11:
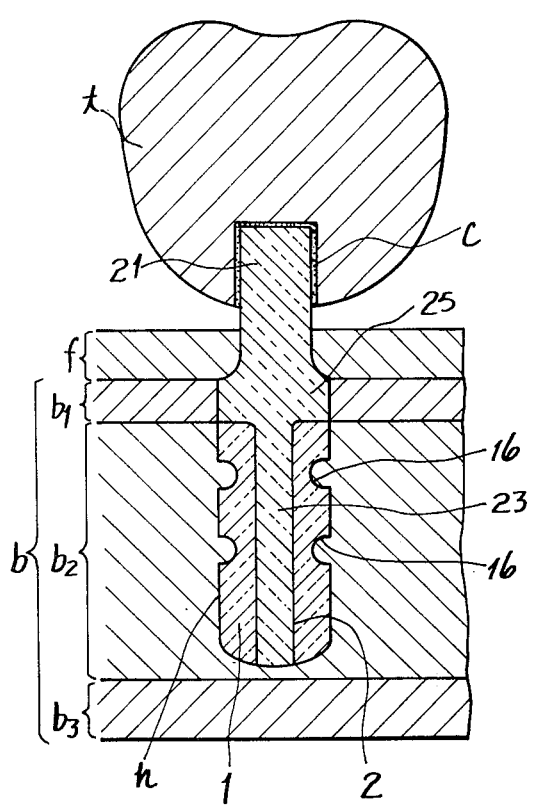
FIG. 11 is a sectional view showing the prosthetic structure of an artificial tooth using the dental pin type implant in still another embodiment of the invention.
Figure 12:
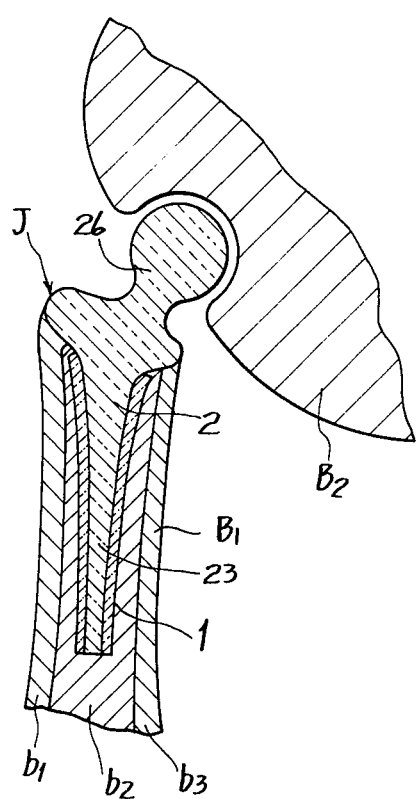
FIG. 12 is a sectional view showing another embodiment of the invention as applied to an artificial hip joint.

EXAMPLE 3 (corresponding to the embodiment in FIG. 11).

(I) Production of outer member (a) Ceramic material—99.5% (by weight and the same will apply hereinafter) of $Al_2O_3$ (99.8% in purity) in powdered form (0.1–1.5 μm in grain diameter) and 0.5% of sintering accelerator MgO.
(b) Pore-forming material—20% of polyethylene spherical body (200–1000 μm in grain diameter) as against 100% of ceramic material.

The above materials (a) and (b) were mixed by a mixer. The mixture of (a) and (b) thus obtained was poured into a dental endosseous implant forming mold and compacted under a pressure of 500 kg/cm/² at normal temperature.

The molded body thus obtained was sintered at a temperature of 1620° C. for two hours. The sintered body thus produced was formed on the surface with openings of micro-apertures between numerous continuous pores, the openings measuring 200–700 μm in diameter. The sintered body was about 30–35% in porosity and was generally a gas-permeable porous polycrystalline sintered body. The periphery of the sintered body was subjected to thread machining, to obtain an outer member.

(II) Production of inner core material

The core material was formed with its post portion having a diameter of 2.5 mm from a single crystal of alumina ceramics by methods well known in the industry.

(III) Bonding of outer member to core member

The core member in (II) was inserted into the outer member in (I) and bonded with a glass cement, the particulars of which are described below. The member thus bonded were sintered into one body at a temperature of 1000°–1600° C. in the open air.

(a) In one embodiment, a glass cement made by the applicant's company having the following chemical composition was used as a cement;

| | |
|---|---|
| $SiO_2$ | 57% (by weight) |
| $B_2O_3$ | 23% |
| $Al_2O_3$ | 2% |
| $Na_2O_3$ | 3% |
| BaO | 7% |
| ZnO | 8% |
| Sum | 100% |

The above mixed cement was mixed with water to form a paste for painting. The coefficient of thermal expansion of the mixture was measured as $60 \times 10^{-7}$ and the sintering conditions utilized to bond the two members was under 1200° C. and 30 minutes.

(b) Another embodiment used a heat resisting $Al_2O_3$ based glass cement in water paste obtained under the trademark of "SUMICERAM" S-208 B (manufactured by the Sumitomo Chemical Company, Ltd.). The exact chemical composition thereof was unknown but the coefficient of thermal expansion of the cement was represented as $65 \times 10^{-7}$ (at 30°–400° C.). The sintering condition utilized with this cement was under 1550° C. for one hour.

The coefficient of thermal expansion of these two cements was consistent with that of $Al_2O_3$, whose coefficient of thermal expansion is $68 \times 10^{-7}$ (at 30°–400° C.).

The implant of Example 3 was used in a prosthetic shown in FIG. 11. An X-ray photograph of the implant taken about six months after the operation showed that primarily new bone tissue has penetrated in large quantities from the surface of the pin deep into the pin.

The joining of the solid inner core member 2 to the porous outer member 1 by interposing a cementing agent such as glass cement between the two and the heating the same at a temperature of 1000°–1600° C. causes the pores existing in the connection between the two members to be filled with molten glass cement, resulting in the connected portions to have an increased area of contact, thereby almost completely precluding a possibility of the solid inner core member from being disconnected from the porous outer member. In addition, the necessity of troublesome machining of the solid inner core member and the porous outer member may be avoided if desired due to the increased strength of the bonding between the two members due to use of the glass cement.

A torque test was carried out with respect to the test samples according to Examples 1, 2 and 3, with the results following.

TORQUE TEST RESULTS

| Sample | Results of Torque Strength (kg-cm) Test | Comments |
|---|---|---|
| Example 3 | 13 kg-cm (Cement a) 10 kg-cm (Cement b) | Inner core member was disconnected from outer member at 13 kg-cm or 10 kg-cm torque. |
| Example 1 | 3 kg-cm | Neck portion of inner core member broke away at under 3 kg-cm torque |
| Example 2 | 0 kg-cm | Inner core member disconnected from outer member immediately after torque was applied to the inner core member |

From the above results is apparent that an implant according to Example 3 is superior in torque strength to that of Examples 1 and 2 in that it substantially eliminates the possibility of the inner core member loosening, or coming out under such external forces as a biting force, a rotational force, etc.

The description above has been of preferred embodiments of the invention, and the invention further includes the following modifications thereof.

(A) A modification in which the outer member is produced not by a method of forming pressure-compacted power but by a slip casting method.

(B) A modification in which the outer and inner core members contain an X-ray non-transmitting agent such as $Y_2O_3$, $ZrO_2$, $La_2O_3$, etc., for facilitating an X-ray examination of the post-operational position of the members.

(C) A modification in which, in the embodiment of the second species containing an apatite sintered body, the apatite sintered body is dissolved by dipping the outer member in an acid such as HCl or $NHO_3$. A porous ceramic outer member having numerous pores is formed by the partial dissolving of the apatite sintered body. There remains undissolved a portions of the apatite component inside the pores formed by such dissolving, this undissolved portion assisting in inducing new bone and connective tissues to penetrate into the member.

(D) A modification in to which the implant may be used for other orthopedic surgical operations such as a prosthetic operation on an arm bone joint, instead of an artificial hip joint.

Having described our invention as related to the embodiments shown in the accompanying drawing, it is our intention that the invention be not limited by any of the details, unless otherwise specified, but rather be construed broadly within its spirit and scope as set forth in the appended claims.

We claim that:

1. A ceramic endosseous implant, comprising:
   a composite structural member having a ceramic outer member of polycrystalline alumina ceramic and a ceramic inner core member of single crystalline alumina ceramic;
   said outer member having a generally cylindrical shape and a cavity with micro-apertures on the outer surface thereof for permitting the penetration of a new bone and connective tissue thereinto;
   said inner member, of alumina ceramic, with a post portion adapted to be inserted in said cavity, a flange portion adjacent said post portion for the covering of said cavity, and a mounting post for use in attaching a prothesis; and said inner core member bonded to said outer member by a heat resistant glass cement having a coefficient of thermal expansion approximating that of alumina ceramic.

2. An implant according to claim 1 wherein said inner core member is made of a single crystalline ceramic.

3. An implant according to claim 1 wherein said cement has a coefficient of thermal expansion approximating that of said inner core member and said outer member.

4. An implant according to claim 1 wherein said cement has the following composition by weight:

| $SiO_2$ | 57% (by weight) |
|---|---|
| $B_2O_3$ | 23% |
| $Al_2O_3$ | 2% |
| $Na_2O_3$ | 3% |
| BaO | 7% |
| ZnO | 8% |
| Total | 100% |

5. An implant according to claim 1 wherein said outer member comprises protuberances on its outer surface to aid in securely engaging surrounding tissue.

6. An implant according to claim 5 wherein said protrusion on said ceramic outer member is an external thread adapted to be threadedly fitted into said tissue.

7. An implant according to claim 5 wherein said protrusions on said ceramic outer member are formed by discontinuous ringlike or helical recesses adapted to engage said tissue.

8. A ceramic endosseous implant according to claim 1 wherein said micro-apertures have a diameter greater than 20 μm.

9. A ceramic endosseous implant according to claim 1 wherein said micro-apertures have a diameter of 20–700 μm.

10. A ceramic endosseous implant according to claim 1 wherein said micro-apertures have a diameter of 500 μm–5 mm.

11. A ceramic endosseous implant according to claim 1 wherein said outer member and said inner member are sintered together.

12. A ceramic endosseous implant according to claim 1 wherein said outer member and said inner member are threaded together.

13. An implant according to claim 1 wherein said cement is a heat-resistant $Al_2O_3$-based cement.

14. A ceramic endosseous implant, comprising:

a composite structural member having a ceramic outer member of polycrystalline alumina ceramic and a ceramic inner core member of single crystalline alumina ceramic;

said outer member, having a generally cylindrical shape and a cavity, manufactured to have material distributed therethrough in a predetermined configuration, said material being degradeable by new bone and connective tissue when said implant is inserted into a living being, forming micro-apertures in said outer member into which said new bone and connective tissue may penetrate;

said inner member of alumina ceramic, configured to reinforce said outer member, with a post portion adapted to be inserted in said cavity, a flange portion adjacent said post portion for the covering of said cavity, and a mounting post for use in attaching a prothesis;

said inner core member bonded to said outer member by a heat resistant glass cement having a coefficient of thermal expansion approximating that of alumina ceramic.

15. A ceramic endosseous implant comprising a composite structural member having a ceramic outer member of polycrystalline alumina ceramic and a ceramic inner core member fused together by a glass cement having a coefficient of thermal expansion approximating that of alumina ceramic, said outer member having micro-apertures on the outer surface thereof for permitting the penetration of new bone and connective tissue thereinto, and said inner member made of single crystalline alumina ceramic and configured to reinforce said outer member.

16. A ceramic endosseous implant according to claim 14 wherein said outer member and said inner core member are threaded together.

17. An implant according to claim 14 wherein said material comprises apatite.

18. A ceramic outer member, having a cavity, for permanent insertion into body tissues, having an outer surface contacting said tissues and formed to encourage the growth of said tissues into said member, and further having a shape to mechanically engage said tissues during said growth;

a single crystalline ceramic inner core member shaped to fill said cavity and to provide an protrusion for attaching a prothesis;

said inner core member permanently affixed to said outer member by a glass cement having coefficient of thermal expansion approximating that of said outer and inner core members.

19. An implant according to claim 18 wherein the outer surface of said outer member contains micro-apertures of size to encourage the growth of said tissues into said apertures.

20. An implant according to claim 19 wherein the size of said micro-apertures are selectively apportioned in accordance with a desired ratio of growth into said apertures of bone and connective tissues to provide an affixation of said member having predetermined proportion of strength and elasticity.

21. An implant according to claim 18 wherein said outer member's outer surface comprises a material able to be degraded and replaced by tissue in contact with said material.

22. An implant according to claim 21 wherein said material comprises apatite.

23. An implant according to claim 18 wherein said cement has penetrated the surfaces of said inner core and outer member in contact with each other and fused said members together.

* * * * *